US012749280B2

(12) United States Patent
Sugahara et al.

(10) Patent No.: US 12,749,280 B2
(45) **Date of Patent: *Sep. 29, 2026**

(54) INFORMATION PROCESSING APPARATUS, INFORMATION PROCESSING METHOD, AND INFORMATION PROCESSING PROGRAM INVOLVING PERFORMING RADIOGRAPHY ON A SUBJECT AFTER SWALLOWING A SAMPLE

(71) Applicant: FUJIFILM CORPORATION, Tokyo (JP)

(72) Inventors: Masataka Sugahara, Tokyo (JP); Koji Taninai, Tokyo (JP); Yuji Jibiki, Tokyo (JP); Tatsuya Taneichi, Tokyo (JP); Hisatsugu Horiuchi, Tokyo (JP)

(73) Assignee: FUJIFILM CORPORATION, Tokyo (JP)

(*) Notice: Subject to any disclaimer, the term of this patent is extended or adjusted under 35 U.S.C. 154(b) by 259 days.

This patent is subject to a terminal disclaimer.

(21) Appl. No.: 18/475,227

(22) Filed: Sep. 27, 2023

(65) Prior Publication Data

US 2024/0112439 A1 Apr. 4, 2024

(30) Foreign Application Priority Data

Sep. 30, 2022 (JP) ................................ 2022-158970

(51) Int. Cl.

*G06T 7/70* (2017.01)
*A61B 6/00* (2006.01)
(Continued)

(52) U.S. Cl.

CPC ................ *G06V 10/25* (2022.01); *A61B 6/52* (2013.01); *G06T 7/0012* (2013.01); *G06T 7/70* (2017.01);
(Continued)

(58) Field of Classification Search

CPC ...... G06V 10/25; G06V 10/14; G06V 40/103; G06V 2201/031; A61B 6/52;
(Continued)

(56) References Cited

U.S. PATENT DOCUMENTS

2008/0279331 A1* 11/2008 Huang ................ A61B 6/4482 378/68
2009/0136000 A1* 5/2009 Nishii ...................... A61B 6/08 378/98.3
(Continued)

FOREIGN PATENT DOCUMENTS

JP H11226006 A * 8/1999
JP 2006-136500 A 6/2006
(Continued)

OTHER PUBLICATIONS

English language translation of the following: Office action dated May 26, 2026 from the JPO in a Japanese patent application No. 2022-158970 corresponding to the instant patent application. This office action translation is submitted now in order to supplement the understanding of the cited references which are being disclosed in the instant Information Disclosure Statement.

*Primary Examiner* — Siamak Harandi
(74) *Attorney, Agent, or Firm* — SOLARIS Intellectual Property Group, PLLC

(57) ABSTRACT

An information processing apparatus comprising at least one processor, wherein the processor is configured to: acquire at least one optical image obtained by optically imaging a subject from a first direction; estimate a position of at least one first region of interest based on the optical image; acquire a plurality of radiation images obtained by continuously performing radiography of a state in which the subject swallows a sample from the first direction; specify a second region of interest corresponding to the position of the first region of interest in the radiation image; monitor a position
(Continued)

of the sample based on the plurality of radiation images; and change an imaging condition for the radiography based on a positional relationship between the second region of interest and the sample.

13 Claims, 11 Drawing Sheets

(51) Int. Cl.
*A61B 6/08* (2006.01)
*G06T 7/00* (2017.01)
*G06V 10/25* (2022.01)

(52) U.S. Cl.
CPC ............... *G06T 2207/10116* (2013.01); *G06T 2207/20044* (2013.01); *G06T 2207/30092* (2013.01)

(58) Field of Classification Search
CPC ....... A61B 6/0407; A61B 6/08; A61B 6/4464; A61B 6/5217; A61B 6/545; G06T 7/0012; G06T 7/70; G06T 2207/10116; G06T 2207/20044; G06T 2207/30092; G06T 7/75
See application file for complete search history.

(56) References Cited

U.S. PATENT DOCUMENTS

| | | | | |
|---|---|---|---|---|
| 2009/0257554 | A1* | 10/2009 | Parks ....................... | A61B 6/12 378/62 |
| 2015/0327833 | A1* | 11/2015 | Tsuchiya ............. | A61B 6/4405 378/91 |
| 2017/0055925 | A1 | 3/2017 | Lee et al. | |
| 2017/0322484 | A1 | 11/2017 | Erhard | |
| 2019/0066260 | A1 | 2/2019 | Christian et al. | |

FOREIGN PATENT DOCUMENTS

| | | | |
|---|---|---|---|
| JP | 2015-009097 | A | 1/2015 |
| JP | 2016-034300 | A | 3/2016 |
| JP | 2017-534401 | A | 11/2017 |

* cited by examiner

INFORMATION PROCESSING APPARATUS, INFORMATION PROCESSING METHOD, AND INFORMATION PROCESSING PROGRAM INVOLVING PERFORMING RADIOGRAPHY ON A SUBJECT AFTER SWALLOWING A SAMPLE

CROSS-REFERENCE TO RELATED APPLICATIONS

This application claims priority from Japanese Application No. 2022-158970, filed on Sep. 30, 2022, the entire disclosure of which is incorporated herein by reference.

BACKGROUND

Technical Field

The present disclosure relates to an information processing apparatus, an information processing method, and an information processing program.

Related Art

In the related, the videofluoroscopic examination of swallowing in which a subject drinks a sample and continuously performs radiography on a state in which the sample passes through the esophagus, the airway, the epiglottis, or the like has been performed. In addition, various technologies for supporting the videofluoroscopic examination of swallowing are known.

For example, JP2006-136500A discloses that X-ray irradiation is started at a high dose on a diagnosis target part in a case in which the inflow of contrast agent is detected in a monitoring imaging region based on image data obtained by performing the X-ray irradiation at a low dose in the vicinity of the diagnosis target part (imaging region for monitoring) of a subject. In addition, for example, JP2015-009097A discloses that switching from an imaging method for a stomach region to an imaging method for an esophagus region is performed based on at least one of the size of the X-ray irradiation range, an imaging mode, or an examination name, and a rotation angle of a top plate about a rotation axis, and an imaging condition corresponding to the switched imaging method is determined.

By the way, swallowing is divided into the oral preparation phase, the oral phase, the pharyngeal phase, and the esophageal phase. In the related art, the method in which radiographic observation of the pharynx during the oral preparation phase, the oral phase, and the pharyngeal phase and endoscope observation of the lower esophagus during the esophageal phase are used is the mainstream method. In recent years, there has been a demand for a technology capable of observing the lower esophagus by radiography in accordance with the pharynx.

SUMMARY

The present disclosure provides an information processing apparatus, an information processing method, and an information processing program capable of supporting imaging of radiation images.

According to a first aspect of the present disclosure, there is provided an information processing apparatus comprising at least one processor, in which the processor is configured to acquire at least one optical image obtained by optically imaging a subject from a first direction, estimate a position of at least one first region of interest based on the optical image, acquire a plurality of radiation images obtained by continuously performing radiography of a state in which the subject swallows a sample from the first direction, specify a second region of interest corresponding to the position of the first region of interest in the radiation image, monitor a position of the sample based on the plurality of radiation images, and change an imaging condition for the radiography based on a positional relationship between the second region of interest and the sample.

According to a second aspect of the present disclosure, in the first aspect, the processor may be configured to specify a body thickness of the subject based on the optical image, and change the imaging condition based on the body thickness.

According to a third aspect of the present disclosure, in the first aspect or the second aspect, the processor may be configured to specify an imaging direction of the subject based on the optical image, and change the imaging condition based on the imaging direction.

According to a fourth aspect of the present disclosure, in any one of the first aspect to the third aspect, the processor may be configured to notify that the imaging condition is changed.

According to a fifth aspect of the present disclosure, in any one of the first aspect to the fourth aspect, the processor may be configured to display the radiation image and a type of the second region of interest in which the sample included in the radiation image is located, on a display in association with each other.

According to a sixth aspect of the present disclosure, in any one of the first aspect to the fifth aspect, the processor may be configured to store the radiation image and a type of the second region of interest in which the sample included in the radiation image is located, in a storage unit in association with each other.

According to a seventh aspect of the present disclosure, in any one of the first aspect to the sixth aspect, the processor may be configured to determine whether the subject is in a forward leaning posture, an upright posture, or a backward leaning posture, based on the optical image, and store the radiation image and a determination result of the posture of the subject in a storage unit in association with each other.

According to an eighth aspect of the present disclosure, in any one of the first aspect to the seventh aspect, the processor may be configured to specify a plurality of joint points of the subject based on the optical image, and estimate the position of the first region of interest based on a relative positional relationship of the plurality of joint points.

According to a ninth aspect of the present disclosure, in any one of the first aspect to the eighth aspect, the first region of interest and the second region of interest may be at least one of a throat, a shoulder, an esophagus, an airway, an epiglottis, or a stomach.

According to a tenth aspect of the present disclosure, in any one of the first aspect to the ninth aspect, the processor may be configured to acquire a second optical image and a second radiation image which are obtained by performing optical imaging and radiography from a second direction that is different from the first direction simultaneously with the optical imaging and the radiography from the first direction, estimate a position of at least one third region of interest based on the second optical image, specify a fourth region of interest corresponding to the position of the third region of interest in the second radiation image, monitor the position of the sample based on the second radiation image, and change the imaging condition for the radiography from at least one of the first direction or the second direction, based on a positional relationship between the fourth region of interest and the sample that is monitored from the second radiation image.

According to an eleventh aspect of the present disclosure, in any one of the first aspect to the tenth aspect, the radiation image may be an image captured by an imaging apparatus in which a distance between a radiation source and a radiation detector is variable, and the processor may be configured to acquire the distance between the radiation source and the radiation detector, and specify the second region of interest in the radiation image based on the distance.

According to a twelfth aspect of the present disclosure, in the eleventh aspect, the imaging apparatus may include a radiation emitting unit of ceiling-mounted type, and the radiation emitting unit may include the radiation source.

According to a thirteenth aspect of the present disclosure, there is provided an information processing method including acquiring at least one optical image obtained by optically imaging a subject from a first direction, estimating a position of at least one first region of interest based on the optical image, acquiring a plurality of radiation images obtained by continuously performing radiography of a state in which the subject swallows a sample from the first direction, specifying a second region of interest corresponding to the position of the first region of interest in the radiation image, monitoring a position of the sample based on the plurality of radiation images, and changing an imaging condition for the radiography based on a positional relationship between the second region of interest and the sample.

According to a fourteenth aspect of the present disclosure, there is provided an information processing program for causing a computer to execute a process including acquiring at least one optical image obtained by optically imaging a subject from a first direction, estimating a position of at least one first region of interest based on the optical image, acquiring a plurality of radiation images obtained by continuously performing radiography of a state in which the subject swallows a sample from the first direction, specifying a second region of interest corresponding to the position of the first region of interest in the radiation image, monitoring a position of the sample based on the plurality of radiation images, and changing an imaging condition for the radiography based on a positional relationship between the second region of interest and the sample.

With the above-described aspects, the information processing apparatus, the information processing method, and the information processing program according to the present disclosure are capable of supporting imaging of radiation images.

DETAILED DESCRIPTION

First Embodiment

Figure 1:
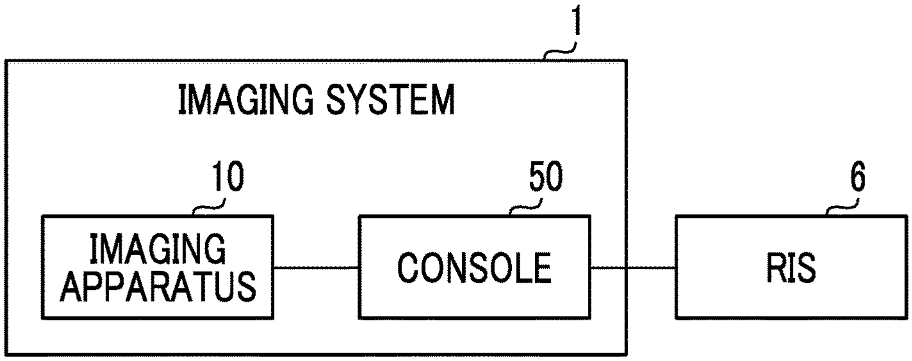
FIG. 1 is a view illustrating an example of a schematic configuration of an imaging system.

In the following, embodiments of the present disclosure will be explained with reference to the drawings. First, a configuration of an imaging system 1 will be explained with reference to FIG. 1. FIG. 1 is a diagram illustrating a schematic configuration of the imaging system 1. As illustrated in FIG. 1, the imaging system 1 comprises an imaging apparatus 10 and a console 50. The imaging apparatus 10 and the console 50, and the console 50 and an external radiology information system (RIS) 6 are configured to be connectable to each other via a wired or wireless network.

The console 50 acquires an imaging order or the like from the RIS 6 and controls the imaging apparatus 10 according to the acquired imaging order, an instruction from a user, and the like. The imaging apparatus 10 captures a radiation image of a subject H according to the control of the console 50. The console 50 is an example of an information processing apparatus of the present disclosure.

Figure 2:
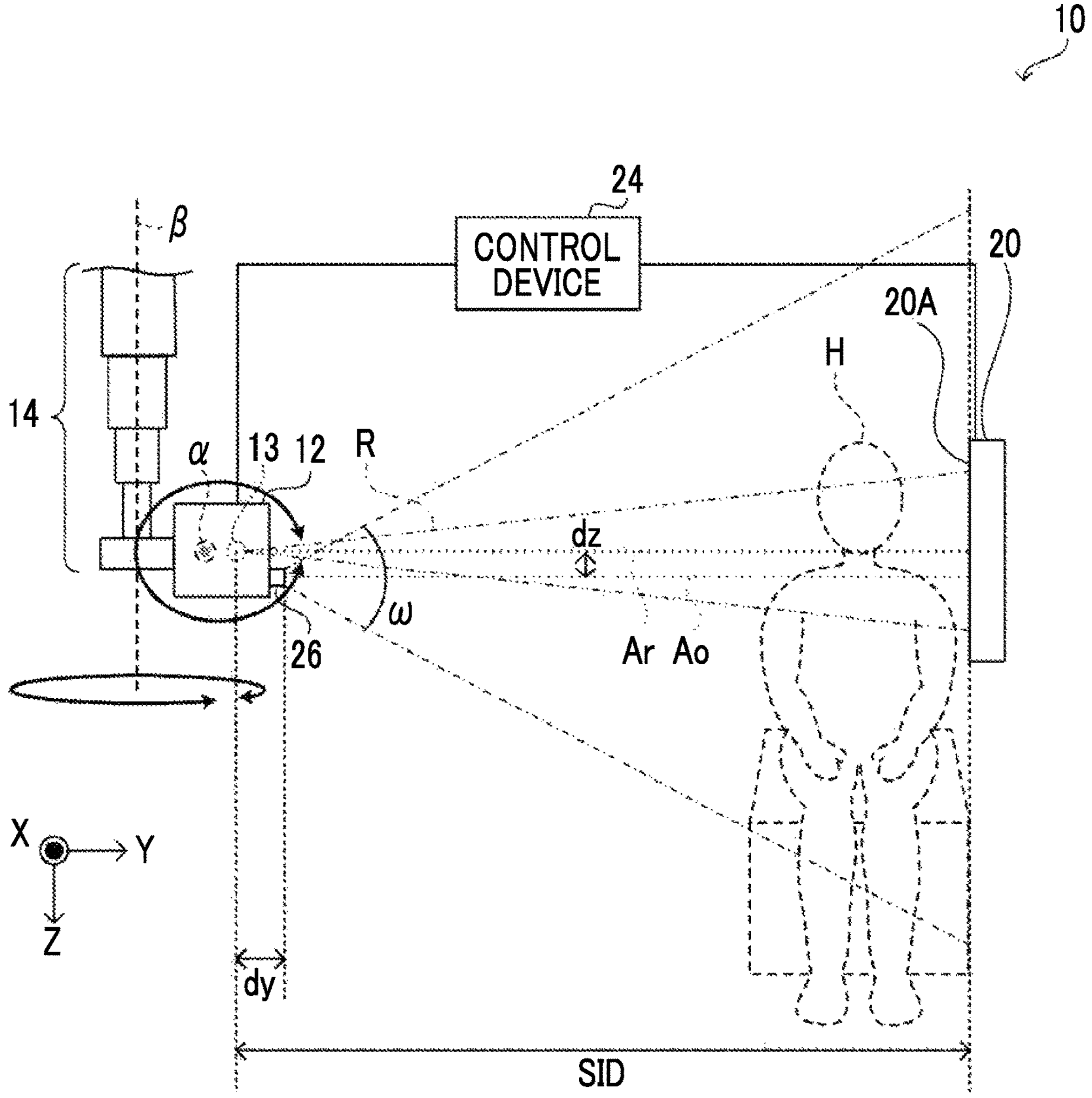
FIG. 2 is a side view illustrating an example of an external appearance of an imaging apparatus.

Next, the imaging apparatus 10 will be explained with reference to FIG. 2. FIG. 2 is a view illustrating a schematic configuration of the imaging apparatus 10. As illustrated in FIG. 2, the imaging apparatus 10 comprises a radiation emitting unit 12, a radiation detector 20, a control device 24, and an optical camera 26.

The radiation emitting unit 12 comprises a radiation source 13 that emits radiation R such as X-rays. In addition, the radiation emitting unit 12 comprises a collimator (not illustrated) and the like, and is configured to change an irradiation field (the range illustrated by the two-dot chain line in FIG. 2) of the radiation R emitted from the radiation source 13. The type of the radiation source 13 is not particularly limited. However, in order to suitably switch the imaging conditions such as the dose (explained in detail in the second embodiment), it is preferable to use a cold cathode type radiation source in which the cathode is composed of carbon nanotubes or the like rather than a hot cathode type radiation source.

In addition, the radiation emitting unit 12 is a so-called radiation emitting unit of ceiling-mounted type that is held by a support column 14 suspended from a ceiling of an imaging room. The support column 14 is attached to rails running around the ceiling via wheels (not illustrated), and is movable in a horizontal direction (X direction and Y direction) in the imaging room. In addition, the support column 14 can be expanded and contracted in a vertical direction (Z direction). In addition, the imaging apparatus 10 comprises a moving mechanism (not illustrated) such as a motor that moves the support column 14 in the horizontal direction and expands and contracts it in the vertical direction. By the movement of the support column 14 in the horizontal direction and the expansion and contraction of the support column 14 in the vertical direction, the radiation emitting unit 12 is also translationally moved in the horizontal direction and the vertical direction.

In addition, the radiation emitting unit 12 is connected to the support column 14 so as to be rotationally movable and is rotationally movable about a rotation axis α extending in the horizontal direction (X direction at a position in FIG. 2). In addition, the radiation emitting unit 12 is rotationally movable about a rotation axis β (that is, about the support column 14) extending in the vertical direction (Z direction). In addition, the imaging apparatus 10 comprises a rotation mechanism (not illustrated) such as a motor that rotationally moves the radiation emitting unit 12 about the rotation axis α and the rotation axis β.

The radiation detector 20 detects the radiation R transmitted through the subject H on a detection surface 20A, generates a radiation image based on the detected radiation R, and outputs image data indicating the generated radiation image. The radiation detector 20 is, for example, a portable electronic cassette, and can be used by being placed on any seat or being held by the subject H. That is, the radiation detector 20 can move to any position in the horizontal direction (the X direction and the Y direction) and the vertical direction (the Z direction) with respect to the radiation emitting unit 12. The following is an explanation assuming that the center of the radiation detector 20 is registered with the irradiation axis Ar of the radiation R emitted from the radiation source 13.

The type of the radiation detector 20 is not particularly limited. For example, the radiation detector 20 may be an indirect conversion type radiation detector that converts the radiation R into light and converts the converted light into electric charge, or may be a direct conversion type radiation detector that directly converts the radiation R into electric charge.

The control device 24 controls the entire operation of the imaging apparatus 10 according to instructions from the console 50 and the user. Specifically, the control device 24 acquires image data indicating the radiation image generated by the radiation detector 20 and outputs the image data to the console 50. In addition, the control device 24 acquires an optical image of the subject H captured by the optical camera 26 and outputs the optical image to the console 50.

The control device 24 is composed of, for example, a central processing unit (CPU), a read only memory (ROM), a random access memory (RAM), a storage medium, an interface (I/F) unit, and an operating unit, which are not illustrated. The control device 24 exchanges various types of information with the console 50 via the I/F unit.

The optical camera 26 is an optical digital camera including a Complementary Metal Oxide Semiconductor (CMOS) type image sensor, a Charge Coupled Device (CCD) type image sensor, or the like, and performs imaging based on the visible light as an example. The optical camera 26 enables the still image capture and the motion picture capture. The optical camera 26 images a region (the range illustrated by the one-dot chain line in FIG. 2) wider than the irradiation field of the radiation R (the range illustrated by the two-dot chain line in FIG. 2), and generates an optical image. In addition, an angle of view w of the optical camera 26 is pre-stored in the storage unit 52.

As illustrated in FIG. 2, an imaging direction of optical imaging by the optical camera 26 and an imaging direction of radiography using the radiation emitting unit 12 and the radiation detector 20 are substantially the same direction. Here, the term "substantially the same direction" includes a deviation to the extent that the registration with the radiation image can be achieved by subjecting image correction (geometric transformation) such as an affine transformation and a projective transformation to the optical image.

The position of the optical camera 26 is not particularly limited, for example, as illustrated in FIG. 2, the optical camera 26 may be attached to substantially the same surface as an irradiation opening of the radiation R of the radiation emitting unit 12, or may be attached to the support column 14, the wall surface of the imaging room, or the like. However, since it is preferable that the entire subject H can be optically imaged in order to specify the joint point, which will be described later, it is preferable that the optical camera 26 is attached to substantially the same surface as the irradiation opening of the radiation R and below the irradiation opening of the radiation R. In addition, it is preferable that an optical axis Ao of the optical camera 26 is substantially parallel to the irradiation axis Ar of the radiation R emitted from the radiation source 13.

In addition, it is assumed that a positional relationship between the radiation source 13 and the optical camera 26 is predetermined. As illustrated in FIG. 2, for example, the positional relationship is represented by an interval dz in the Z direction and an interval dx (not illustrated) in the X direction between the irradiation axis Ar of the radiation R emitted from the radiation source 13 and the optical axis Ao of the optical camera 26, and an interval dy in the Y direction between the radiation source 13 and the optical camera 26. In addition, the intervals dx, dy, and dz representing these positional relationships are pre-stored in the storage unit 52.

By the way, in the videofluoroscopic examination of swallowing in which the subject H drinks the sample and continuously performs radiography on a state in which the sample passes through the esophagus, the airway, the epiglottis, or the like has been performed, it is desired to continuously capture the radiation images at a frame rate corresponding to the movement of the sample. In order to improve the frame rate corresponding to the movement of the sample, it is conceivable to reduce the resolution of the radiation image. However, in a case in which radiography is performed with a reduced resolution, the position of the region of interest in the radiation image becomes unclear, and there is a possibility that the esophagus and the airway cannot be distinguished in, for example, the videofluoroscopic examination of swallowing.

Therefore, the console 50 according to the present embodiment supports the imaging of the radiation image by estimating the position of the region of interest in the radiation image based on the optical image obtained by the optical camera 26. In the following, the console 50 will be explained. In the following explanation, a form example in which a radiation image is obtained by radiography of a state in which the subject swallows the sample will be explained.

Figure 3:
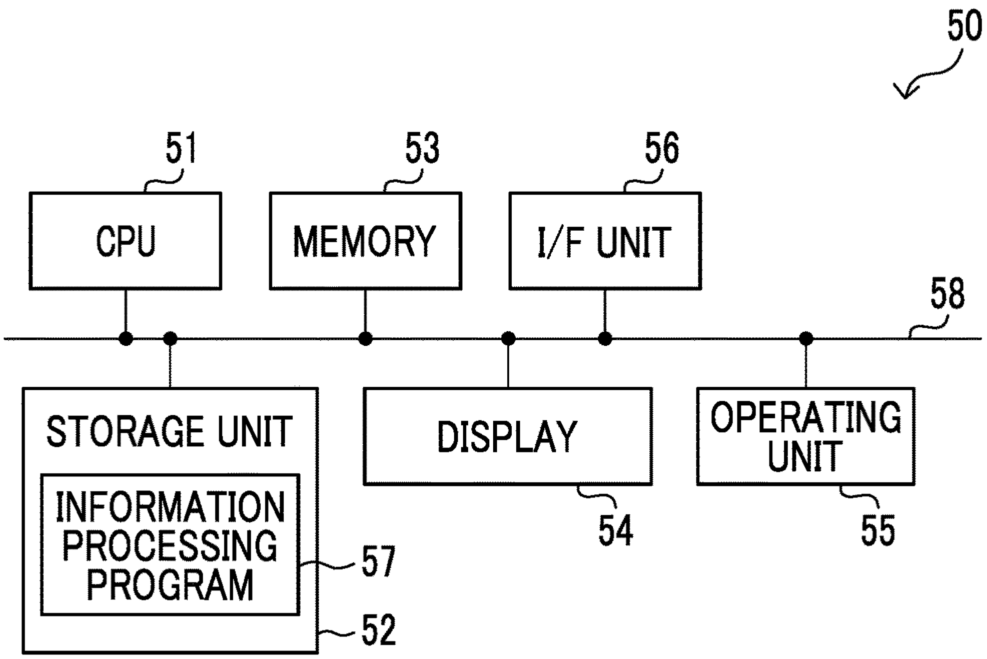
FIG. 3 is a block diagram illustrating an example of a hardware configuration of a console.

First, an example of a hardware configuration of the console 50 will be explained with reference to FIG. 3. As illustrated in FIG. 3, the console 50 includes a central processing unit (CPU) 51, a non-volatile storage unit 52, and a memory 53 as a temporary storage region. In addition, the console 50 includes a display 54 such as a liquid crystal display, an operating unit 55 such as a touch panel, a keyboard, and a mouse, and an interface (I/F) unit 56. The I/F unit 56 performs wired or wireless communication with the imaging apparatus 10, the RIS 6, and other external devices. The CPU 51, the storage unit 52, the memory 53, the display 54, the operating unit 55, and the I/F unit 56 are connected to each other via a bus 58 such as a system bus and a control bus such that various types of information can be exchanged.

The storage unit 52 is realized by, for example, a storage medium such as a hard disk drive (HDD), a solid state drive (SSD), and a flash memory. In the storage unit 52, an information processing program 57 in the console 50 is stored. The CPU 51 reads out the information processing program 57 from the storage unit 52, develops the information processing program 57 into the memory 53, and executes the developed information processing program 57. The CPU 51 is an example of a processor of the present disclosure. For example, a personal computer, a server computer, a smartphone, a tablet terminal, a wearable terminal, or the like can be appropriately applied as the console 50.

Figure 4:
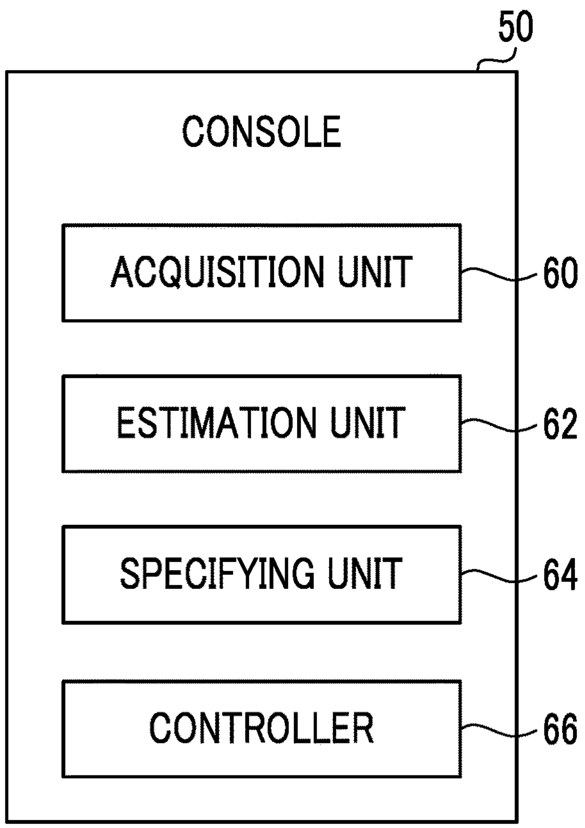
FIG. 4 is a block diagram illustrating an example of a functional configuration of the console.

Next, an example of a functional configuration of the console 50 will be explained with reference to FIG. 4. As illustrated in FIG. 4, the console 50 includes an acquisition unit 60, an estimation unit 62, a specifying unit 64, and a controller 66. In a case in which the CPU 51 executes the information processing program 57, the CPU 51 functions as each functional unit of the acquisition unit 60, the estimation unit 62, the specifying unit 64, and the controller 66.

The acquisition unit 60 acquires at least one optical image obtained by optically imaging the subject H by the optical camera 26 from the control device 24 of the imaging apparatus 10. The estimation unit 62 estimates a position of at least one first region of interest based on the optical image acquired by the acquisition unit 60. In the case of the videofluoroscopic examination of swallowing, the first region of interest is at least one of the throat, shoulder, esophagus, airway, epiglottis, or stomach.

Figure 5:
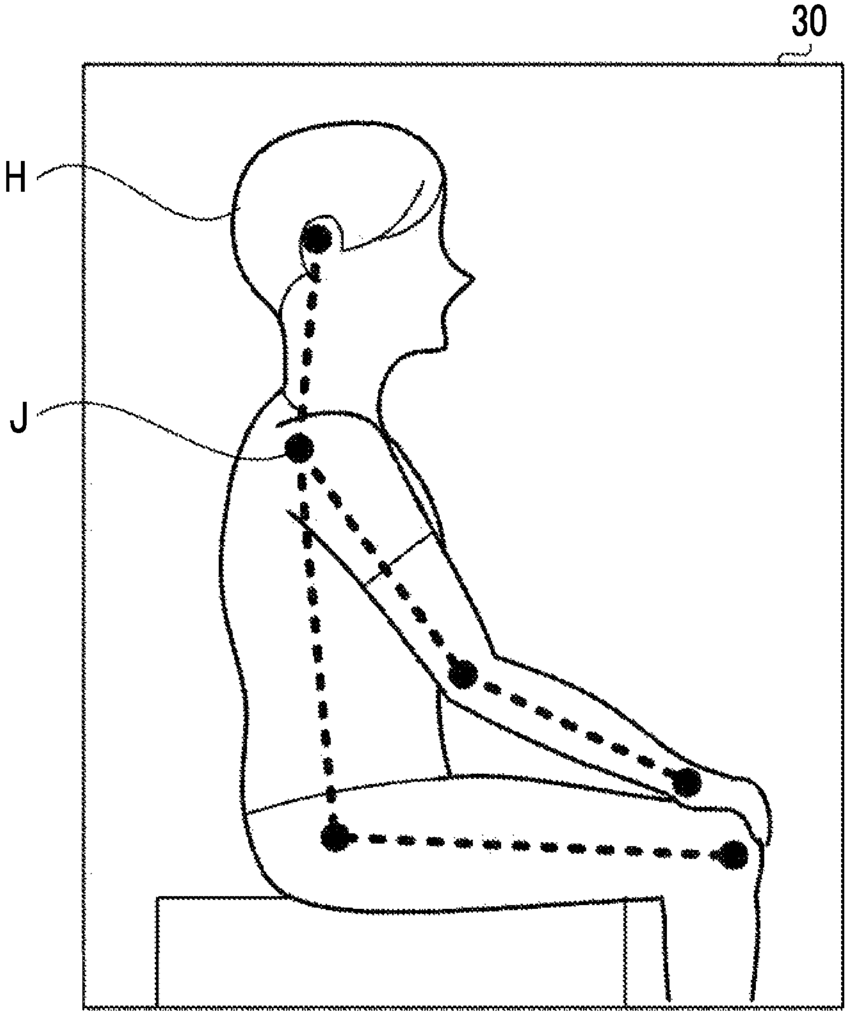
FIG. 5 is a view illustrating an example of an optical image.

FIG. 5 shows an example of an optical image 30 acquired by the acquisition unit 60. Specifically, the estimation unit 62 first specifies a plurality of joint points J of the subject H, such as the ear, shoulder, elbow, wrist, waist, and knee, based on the optical image 30. As a method for specifying joint points, a known posture estimation technology or the like can be appropriately applied.

Figure 6:
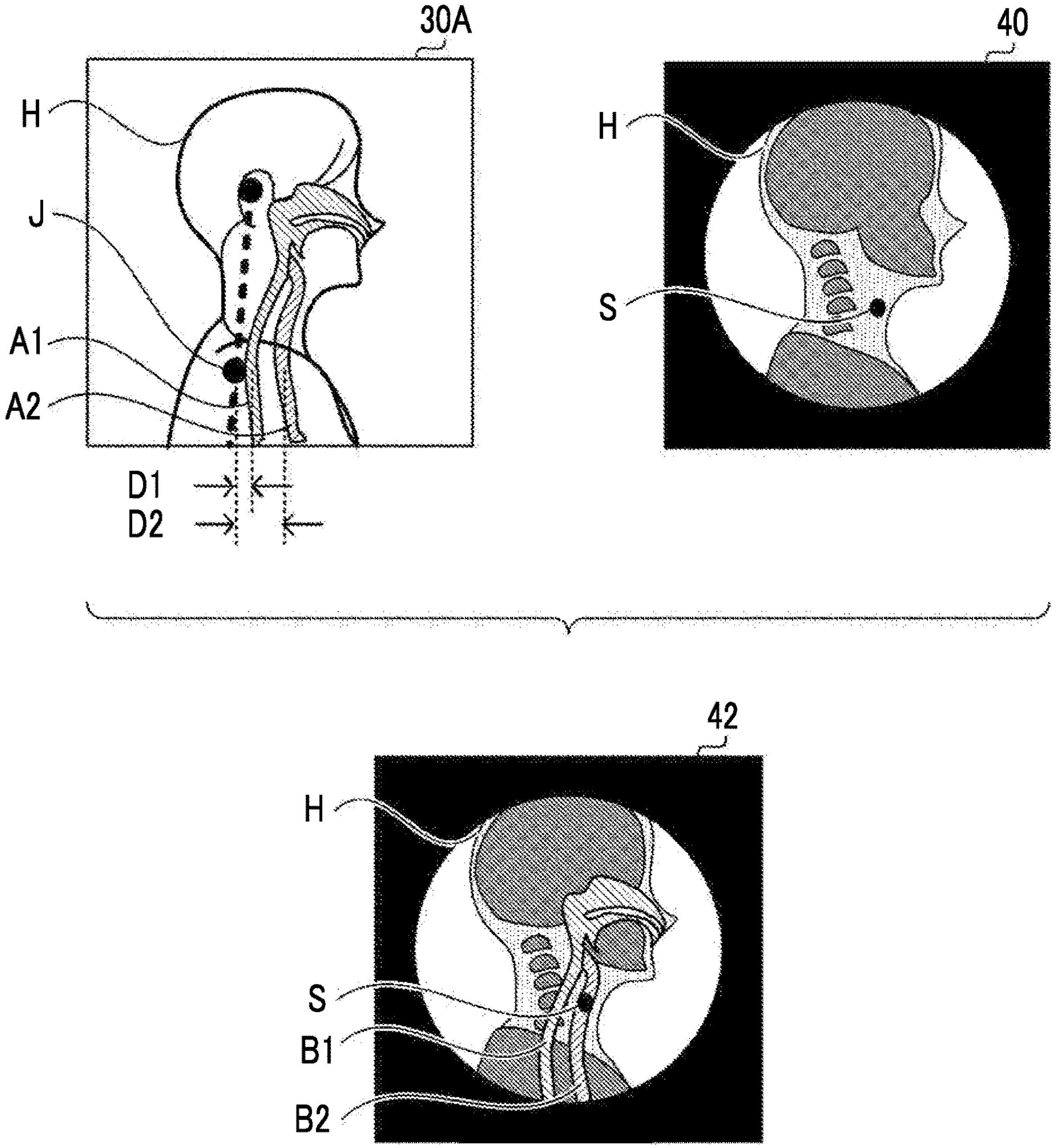
FIG. 6 is a view for explaining a method for specifying a second region of interest in a radiation image.

Then, the estimation unit 62 estimates the position of the first region of interest in the optical image 30, based on the relative positional relationship of the plurality of specified joint points J. FIG. 6 shows a partial view 30A of the optical image 30 in which an esophagus A1 and an airway A2 are estimated as an example of the first region of interest. The positional relationship and a ratio between each joint point J and the esophagus A1 and the airway A2 can be anatomically estimated. For example, as illustrated in FIG. 6, the estimation unit 62 may estimate that the esophagus A1 is located at a position where a distance from the joint point J specified as the shoulder is D1, and the airway A2 is located at a position where a distance from the joint point J specified as the shoulder is D2. In this way, the estimation unit 62 may estimate positions of the plurality of first regions of interest (the esophagus A1 and the airway A2) based on the optical image 30.

In addition, in a case in which the joint point J cannot be specified and the first region of interest cannot be estimated at this point, it is considered that the posture, positioning, and the like of the subject H are not appropriate. Therefore, the estimation unit 62 may notify of the fact (for example, performing control to display on the display 54) and prompt the subject H to set an appropriate posture and positioning.

In addition, the acquisition unit 60 acquires at least one radiation image obtained by radiography of the subject H from the control device 24 of the imaging apparatus 10. FIG. 6 shows an example of a radiation image 40 acquired by the acquisition unit 60. As illustrated in FIG. 6, in the radiation image 40, it is unclear whether a sample S is introduced into the esophagus or the airway.

The specifying unit 64 specifies a second region of interest corresponding to the position of the first region of interest (the esophagus A1 and the airway A2) estimated by the estimation unit 62 in the radiation image 40 acquired by the acquisition unit 60. In addition, in a case in which the positions of the plurality of first regions of interest are estimated by the estimation unit 62, the specifying unit 64 specifies a plurality of second regions of interest corresponding to respective positions of the plurality of first regions of interest in the radiation image 40. In the case of the videofluoroscopic examination of swallowing, similar to the first region of interest described above, the second region of interest is at least one of the throat, the shoulder, the esophagus, the airway, the epiglottis, or the stomach.

Specifically, the specifying unit 64 first registers the optical image 30 and the radiation image 40. For example, the specifying unit 64 acquires a Source to Image receptor Distance (SID), which is a distance between the radiation source 13 and the detection surface 20A of the radiation detector 20. In addition, the specifying unit 64 may register the optical image 30 and the radiation image 40 by geometric calculation using the SID, the positional relationship (intervals dx, dy, and dz) between the radiation source 13 and the optical camera 26 stored in the storage unit 52, the angle of view w of the optical camera 26, and the like. A value of the SID may be measured by, for example, a distance-measuring sensor, or in a case of an imaging apparatus in which the SID is invariable, a predetermined value may be stored in the storage unit 52 or the like. In addition, for example, a marker for SID measurement is provided in the radiation detector 20, and the specifying unit 64 may measure the SID based on the marker included in the optical image 30 obtained by imaging the radiation detector 20 by the optical camera 26.

After the registration of the optical image 30 and the radiation image 40, the specifying unit 64 specifies a region in the radiation image 40 at the same position as the first region of interest in the optical image 30 as the second region of interest. FIG. 6 illustrates the superimposed image 42 in which, in the radiation image 40, the regions at the same positions as the esophagus A1 and the airway A2 in the partial view 30A are specified as an esophagus B1 and an airway B2 as an example of the second region of interest, and these are superimposed on the radiation image 40. It can be seen from the superimposed image 42, the sample S is introduced into the airway B2 side.

In addition, the specifying unit 64 may specify the position of the sample S in the radiation image 40, and may determine that the sample S is introduced into any of the esophagus B1 and the airway B2 based on the position of the second region of interest (the esophagus B1 and the airway B2) and the position of the sample S. The position of the sample S may be specified using, for example, a known pattern matching technology or the like.

As described above, in the videofluoroscopic examination of swallowing, a plurality of radiation images are continuously captured at a frame rate corresponding to the type of the sample. In this case, the acquisition unit 60 may acquire a plurality of radiation images obtained by continuously performing radiography of the subject H. In addition, the specifying unit 64 may specify the second region of interest and a position of the sample S in each of the plurality of radiation images acquired by the acquisition unit 60. Furthermore, the specifying unit 64 may select a part of the radiation image including the timing at which the sample S is introduced into the esophagus B1 or the airway B2 among the plurality of radiation images based on the position of the specified second region of interest and the position of the sample S.

Figure 7:
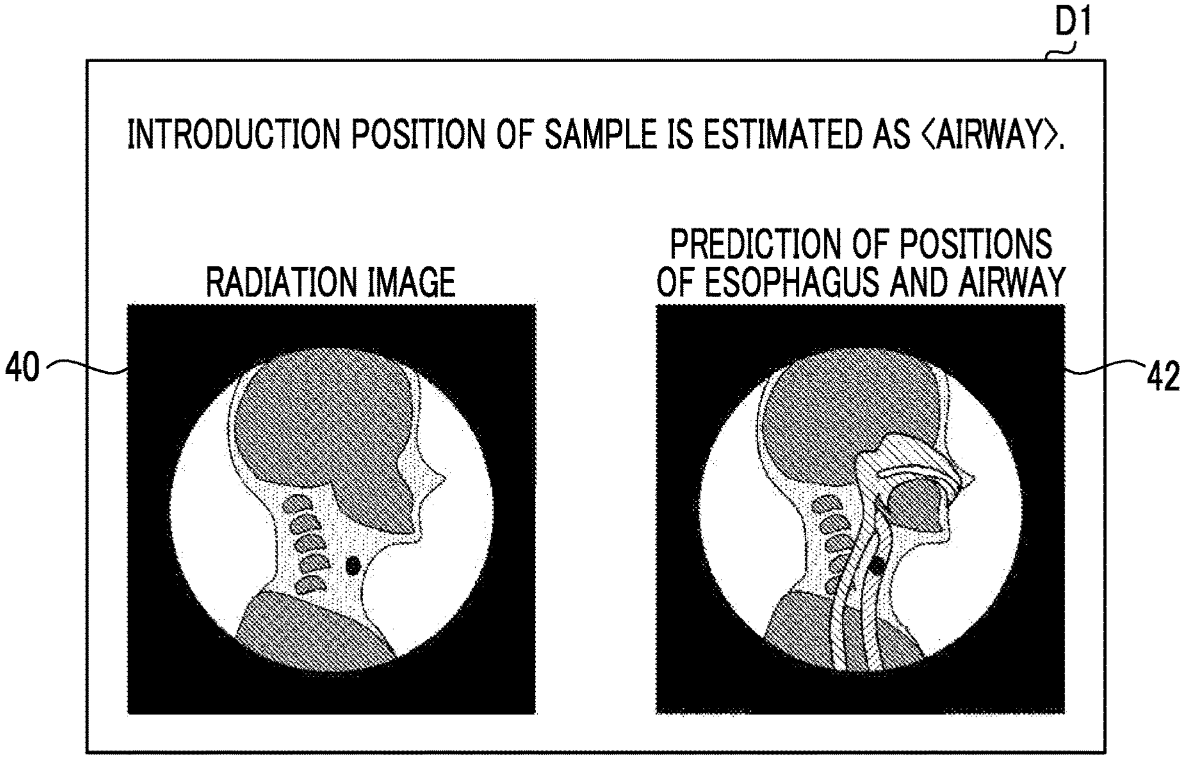
FIG. 7 is a view illustrating an example of a screen displayed on a display.

The controller 66 performs control to display the second region of interest (the esophagus B1 and the airway B2) in the radiation image 40 specified by the specifying unit 64, on the display 54. FIG. 7 is an example of a screen D1 displayed on the display 54 by the controller 66. The screen D1 includes the radiation image 40 and the superimposed image 42 on which the second region of interest (the esophagus B1 and the airway B2) is superimposed on the radiation image 40. By confirming the superimposed image 42, the user can easily confirm the position of the second region of interest (the esophagus B1 and the airway B2) in the radiation image 40.

In addition, in a case in which a part of the radiation image including the timing at which the sample S is introduced into the esophagus B1 or the airway B2 is selected by the specifying unit 64 from among the plurality of continuously captured radiation images, the controller 66 may perform control to display the selected radiation image preferentially on the display 54.

In addition, in a case in which it is determined by the specifying unit 64 whether the sample S is introduced into the esophagus B1 or the airway B2, the controller 66 may perform control to display the determination result on the display 54. That is, even the controller 66 may display the radiation image 40 and the type of the second region of interest (the esophagus or the airway) in which the sample S included in the radiation image 40 is located on the display 54 in association with each other. The screen D1 of FIG. 7 includes a message that an introduction position of the sample S is estimated to be the airway.

In addition, in a case in which the radiation image 40 is stored in various storage units such as the storage unit 52 and an external database, the controller 66 may store the radiation image 40 and the type of the second region of interest (the esophagus or the airway) in which the sample S included in the radiation image 40 is located in the storage unit in association with each other.

In addition, the controller 66 may also control to read out (generate the radiation image) a partial region in the radiation image 40 under a readout condition different from other regions, based on the second region of interest in the radiation image 40 specified by the specifying unit 64. The readout condition is, for example, in the radiation detector 20, a binning size in binning processing in which charges generated by a plurality of adjacent pixels are combined and read out, a charge read interval (a frame rate), a correction amount for gain correction, and the like.

Figure 8:
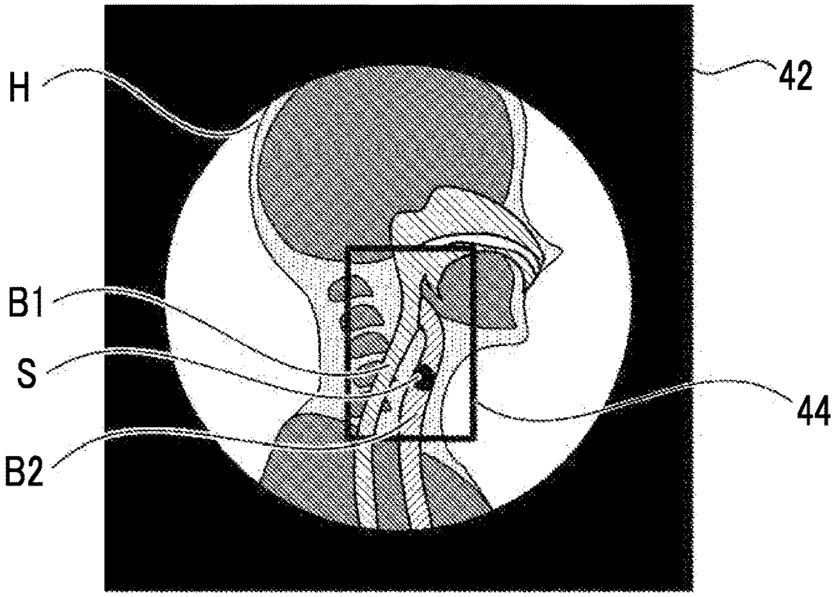
FIG. 8 is a view for explaining processing of changing a readout condition according to the second region of interest.

For example, as illustrated in FIG. 8, the controller 66 designates a partial region 44 including the esophagus B1 and the airway B2, and gives an instruction to the control device 24 of the imaging apparatus 10 so that the binning size is smaller (that is, the resolution is higher) than the other regions. The control device 24 controls the binning size of each pixel in the radiation detector 20 in response to the instruction from the controller 66. For example, in a case in which a pixel size in the radiation detector 20 is 150 μm, the partial region 44 may have 1×1 binning (0.15 mm×0.15 mm) or 2×2 binning (0.3 mm×0.3 mm), and the other regions may have 3×3 binning (0.45 mm×0.45 mm) or 4×4 binning (0.6 mm×0.6 mm).

In addition, for example, the controller 66 may designate a partial region 44 including the esophagus B1 and the airway B2 and give an instruction to the control device 24 of the imaging apparatus 10 so that the partial region 44 has a higher frame rate than the other regions. The control device 24 controls the reading interval of the charge of each pixel in the radiation detector 20 in response to the instruction from the controller 66. For example, the partial region 44 may generate an image like a motion picture at a high frame rate, while the other regions may generate an image like a still image at a low frame rate.

In addition, in a case in which the plurality of second regions of interest are specified by the specifying unit 64, the controller 66 may control reading (generating a radiation image) under different readout conditions for each second region of interest. For example, in the example of FIG. 8, the controller 66 may give an instruction to the control device 24 of the imaging apparatus 10 so that the binning size is smaller and the frame rate is higher in the airway B2 in which the sample S is located, among the esophagus B1 and the airway B2 than in the esophagus B1.

In addition, in a case in which the plurality of second regions of interest are specified by the specifying unit 64, the controller 66 may perform different image processing for each second region of interest in the radiation image. For example, in a case in which radiation images including the stomach in addition to the oral preparation phase, the oral phase, the pharyngeal phase, and the esophageal phase are captured, the stomach can be specified as the second region of interest in addition to the esophagus and the airway. In this case, the controller 66 may perform different image processing on the regions of the esophagus and airway and the region of the stomach in one radiation image. The image processing is, for example, processing of changing the gradation so that each second region of interest can be easily seen.

Figure 9:
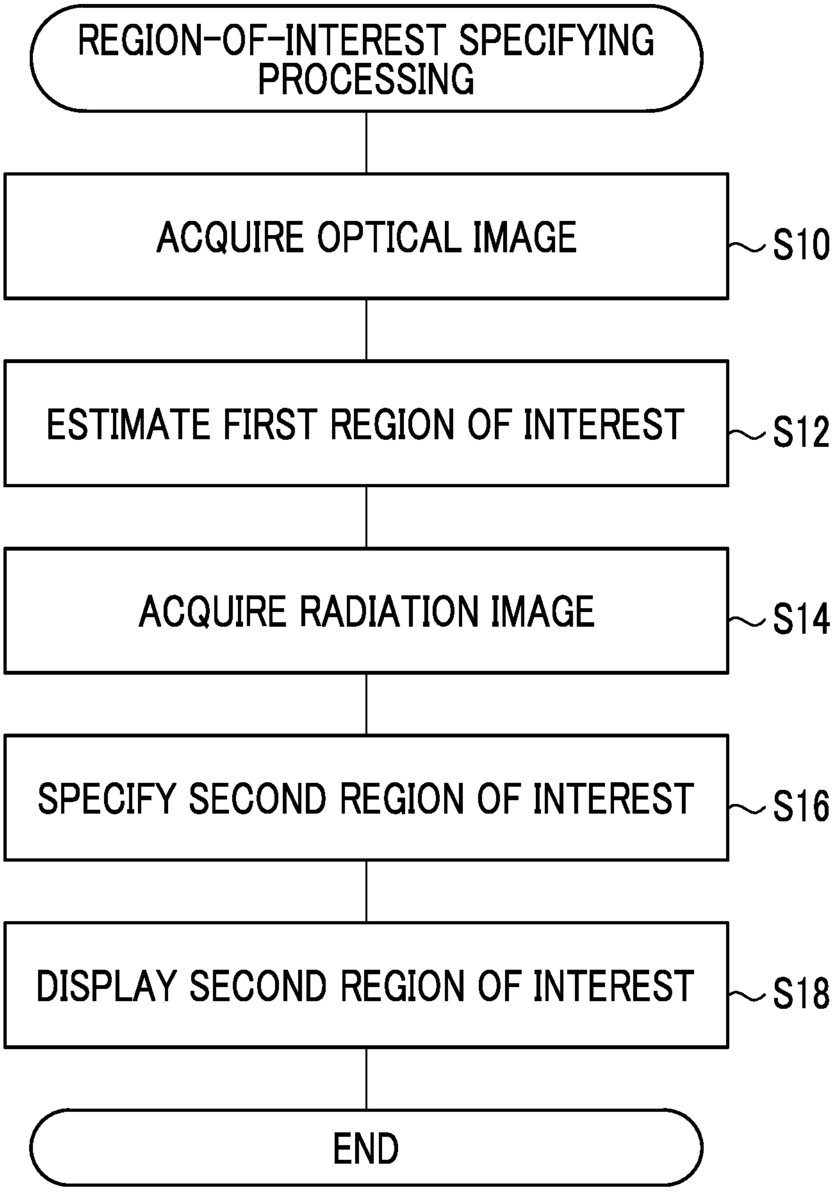
FIG. 9 is a flowchart illustrating an example of region-of-interest specifying processing.

Next, an action of the console 50 according to the present embodiment will be explained with reference to FIG. 9. In the console 50, the CPU 51 executes the information processing program 57 to execute region-of-interest specifying processing illustrated in FIG. 9. The region-of-interest specifying processing is executed, for example, in a case in which the user gives an instruction to start execution via the operating unit 55.

In step S10, the acquisition unit 60 acquires the optical image of the subject H imaged by the optical camera 26 of the imaging apparatus 10. In step S12, the estimation unit 62 estimates the position of at least one first region of interest, based on the optical image of the subject H acquired in step S10.

In step S14, the acquisition unit 60 acquires the radiation image of the subject H, which is captured by the imaging apparatus 10. In step S16, the specifying unit 64 specifies the second region of interest corresponding to the position of the first region of interest estimated in step S12 in the radiation image acquired in step S14. In step S18, the controller 66 controls to display the second region of interest specified in step S16 (such as by superimposing it on the radiation image 40) on the display 54, and ends the main region-of-interest specifying processing.

As explained above, the console 50 according to an aspect of the present disclosure comprises at least one processor, in which the processor is configured to acquire at least one optical image obtained by optically imaging the subject H, acquire at least one radiation image obtained by radiography of the subject H from a direction substantially the same as an imaging direction of the optical imaging, estimate a position of at least one first region of interest based on the optical image, and specify a second region of interest corresponding to the position of the first region of interest in the radiation image.

That is, with the console 50 according to the present embodiment, the position of the region of interest can be estimated based on the optical image even in a case in which the position of the region of interest cannot be specified by the radiation image alone, so that the interpretation of the radiation image can be supported. As a result, it is permissible to reduce the resolution of the radiation image, so that imaging at a high frame rate capable of following the movement of the sample can be realized, for example, in the videofluoroscopic examination of swallowing.

Figure 10:
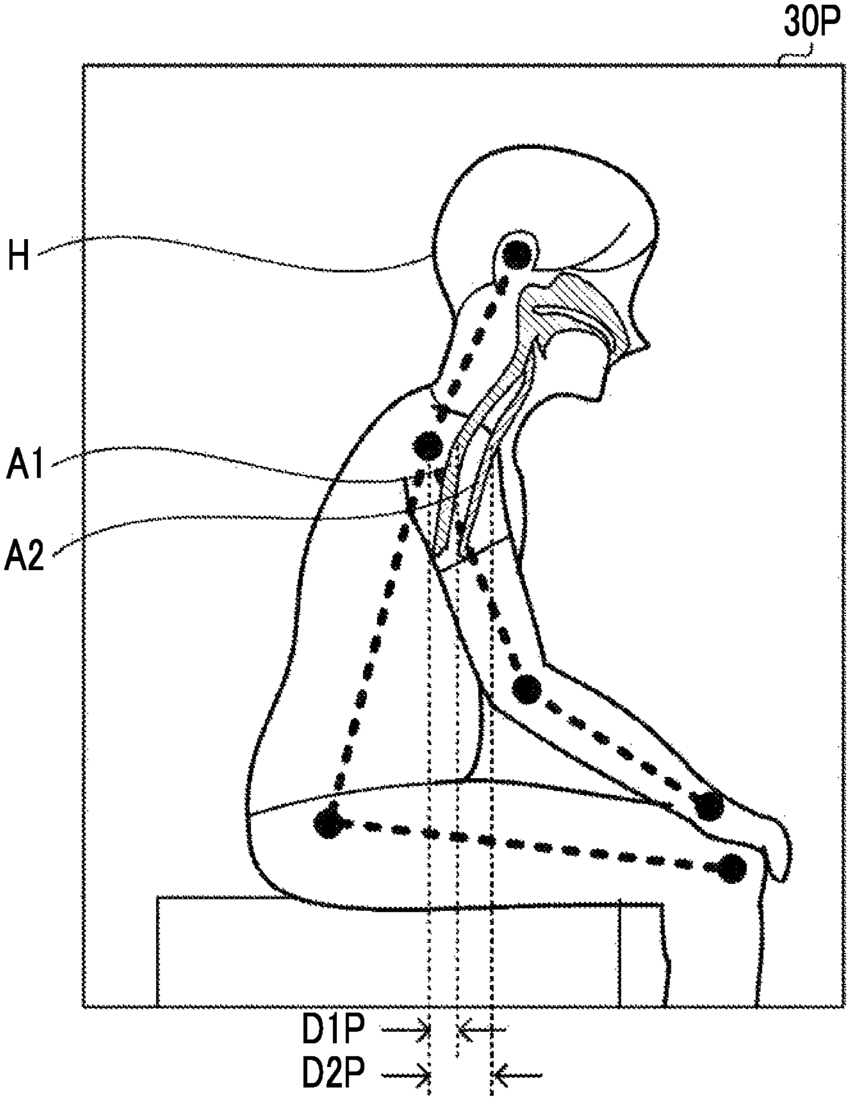
FIG. 10 is a view illustrating an example of an optical image of a forward leaning posture.
Figure 11:
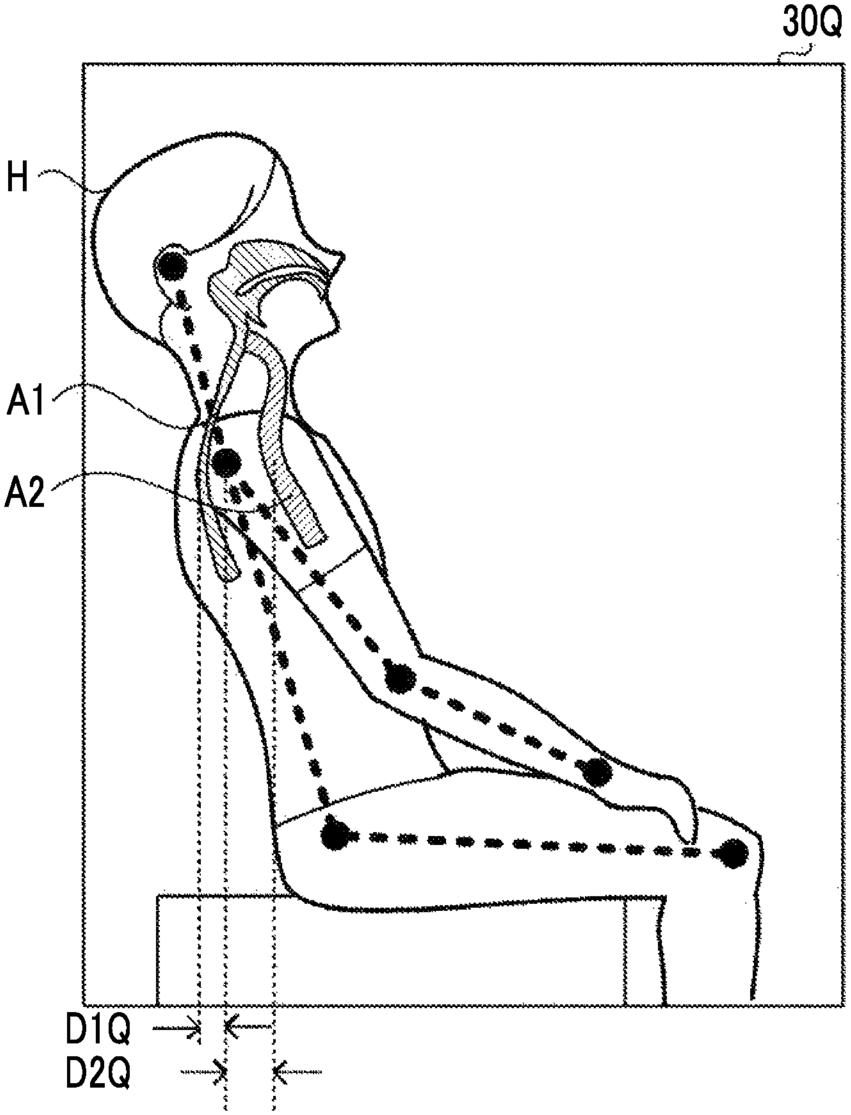
FIG. 11 is a view illustrating an example of an optical image of a backward leaning posture.

In the above-described embodiment, the estimation unit 62 may estimate (correct) the position of the first region of interest in the optical image 30 in consideration of the posture, the body shape, and the like of the subject H. For example, as illustrated in an optical image 30P of FIG. 10, in a case in which the subject H is in a forward leaning posture, the airway A2 may be narrowed due to a relationship between the movement of the spine and gravity. In addition, for example, as illustrated in an optical image 30Q of FIG. 11, in a case in which the subject H is in a backward leaning posture, the esophagus A1 may retreat and the interval from the airway A2 may be widened. In the videofluoroscopic examination of swallowing, there is a case in which the posture is intentionally changed from the upright posture for imaging.

Therefore, the estimation unit 62 may estimate the posture of the subject H based on the relative positional relationship of the plurality of specified joint points J. Specifically, the estimation unit 62 may determine whether the subject H is in the forward leaning posture, the upright posture, or the backward leaning posture, based on the optical image acquired by the acquisition unit 60. In addition, the estimation unit 62 may also estimate the position of the first region of interest according to the estimated posture. For example, in the example of the upright posture in FIG. 6, although a distance from the joint point J of the shoulder to the esophagus A1 is D1, and a distance from the joint point J of the shoulder to the airway A2 is D2, in a case of the forward leaning posture and the backward leaning posture, these distances may be different values. In the example of the forward leaning posture in FIG. 10, the distance from the joint point J of the shoulder to the esophagus A1 is set to D1P, and the distance from the joint point J of the shoulder to the airway A2 is set to D2P. In the example of the backward leaning posture in FIG. 11, the distance from the joint point J of the shoulder to the esophagus A1 is set to D1Q, and the distance from the joint point J of the shoulder to the airway A2 is set to D2Q.

In addition, for example, it is considered that the positional relationship between the esophagus A1 and the airway A2 is different depending on the body thickness. For example, it is considered that a person having a thick body has a larger distance D1 from the joint point J of the shoulder to the esophagus A1 and a larger distance D2 from the joint point J of the shoulder to the airway A2 than a person having a thin body. Therefore, the estimation unit 62 may specify the body thickness of the subject H based on the optical image, and estimate the position of the first region of interest according to the specified body thickness. The body thickness may be estimated based on, for example, the relative positional relationship of the plurality of joint points J, or may be estimated based on the optical image 30 using a known segmentation technology.

In addition, in a case in which the radiation image 40 is stored in various storage units such as the storage unit 52 and an external database, the controller 66 may store the radiation image 40 and the determination result of the posture of the subject H in the storage unit in association with each other. In addition, the controller 66 may store the radiation image 40 and the body thickness of the subject H in association with each other, in the storage unit.

Second Embodiment

By the way, swallowing is divided into the oral preparation phase, the oral phase, the pharyngeal phase, and the esophageal phase. In the related art, the method in which radiographic observation of the pharynx during the oral preparation phase, the oral phase, and the pharyngeal phase and endoscope observation of the lower esophagus during the esophageal phase are used is the mainstream method. In recent years, there has been a demand for a technology capable of observing the lower esophagus by radiography in accordance with the pharynx, but since the lower esophagus is covered by the shoulder with a thick body thickness, it is preferable to use a higher dose than that of the pharynx in order to image it. On the other hand, it is not preferable to irradiate the pharynx with the same dose as that of the lower esophagus because the exposure dose increases.

Therefore, the console 50 according to the present embodiment supports the imaging of the radiation image by appropriately switching the imaging conditions such as the dose with the shoulder as a boundary. Hereinafter, the console 50 will be explained, but a part of the explanation overlapping with the first embodiment will be omitted.

Similar to the first embodiment, the acquisition unit 60 acquires at least one optical image obtained by optically imaging the subject H from a first direction. The estimation unit 62 estimates a position of at least one first region of interest based on the optical image acquired by the acquisition unit 60. Specifically, first, the estimation unit 62 may specify the plurality of joint points J of the subject H based on the optical image, and estimate the position of the first region of interest based on the relative positional relationship of the plurality of joint points J (refer to FIG. 5 and FIG. 6). In the present embodiment, the first region of interest is the shoulder of the subject H.

After the position of the first region of interest (the shoulder) is estimated based on the optical image as described above, the subject H drinks the sample S and starts continuous imaging of the radiation image. The acquisition unit 60 acquires, from the same first direction as the optical image, a plurality of radiation images obtained by continuously performing radiography of a state in which the subject H swallows the sample S.

The specifying unit 64 specifies the second region of interest corresponding to the position of the first region of interest (the shoulder) estimated by the estimation unit 62 in the plurality of radiation images acquired by the acquisition unit 60. That is, the specifying unit 64 specifies a region of the shoulder in the radiation image. In addition, the specifying unit 64 monitors the position of the sample S based on the plurality of radiation images acquired by the acquisition unit 60. That is, the specifying unit 64 specifies the position of the sample S for each of the plurality of radiation images. The specifying of the second region of interest and the position of the sample S by the specifying unit 64 is performed in real time in parallel with the acquisition of the continuous radiation images by the acquisition unit 60.

The controller 66 controls to change the imaging conditions for the radiography based on the positional relationship between the second region of interest (the shoulder) specified by the specifying unit 64 and the sample S. The imaging conditions may be, for example, a tube voltage (kV) of the radiation source 13, a tube current (mA), an imaging time (seconds), a dose (mGy or mSv), a tube current-time product (mAs value), a focal size (large or small focus), an irradiation field size, and the type of the additional filter (such as rhodium, aluminum, and molybdenum), and the like. In addition, for example, the readout condition (such as a binning size, a frame rate, and a correction amount for gain correction) of the radiation detector 20 may be used, or the image processing (gradation change or the like) subjected to the radiation image may be used. For example, the controller 66 may give an instruction to the imaging apparatus 10 to increase the dose when the sample S has entered the second region of interest (the shoulder).

In addition, for example, a person having a thick body is considered to receive a higher appropriate dose than a person having a thin body. Therefore, the specifying unit 64 may specify the body thickness of the subject H, based on the optical image acquired by the acquisition unit 60. The controller 66 may change the imaging conditions based on the body thickness specified by the specifying unit 64. The controller 66 may change an initial value of the imaging condition (that is, the imaging condition in the imaging of the pharynx) based on the body thickness, or may change the imaging condition (that is, the imaging condition in the imaging of the lower esophagus) after the change based on the positional relationship between the second region of interest and the sample S.

In addition, for example, although FIG. 2 illustrates an example of radiography from the side surface side of the subject H, in particular, in a case of confirming a swallowing state in the vicinity of the stomach, radiography may be performed from the front surface side of the subject H. Therefore, the specifying unit 64 may specify the imaging direction of the subject H, based on the optical image acquired by the acquisition unit 60. For example, the specifying unit 64 may specify whether the subject H captured in the optical image faces the side surface or the front surface, based on the relative positional relationship of the plurality of joint points specified by the estimation unit 62. The controller 66 may change the imaging conditions based on the imaging direction specified by the specifying unit 64. The controller 66 may change an initial value of the imaging condition (that is, the imaging condition in the imaging of the pharynx) based on the imaging direction, or may change the imaging condition (that is, the imaging condition in the imaging of the lower esophagus) after the change based on the positional relationship between the second region of interest and the sample S.

Figure 12:
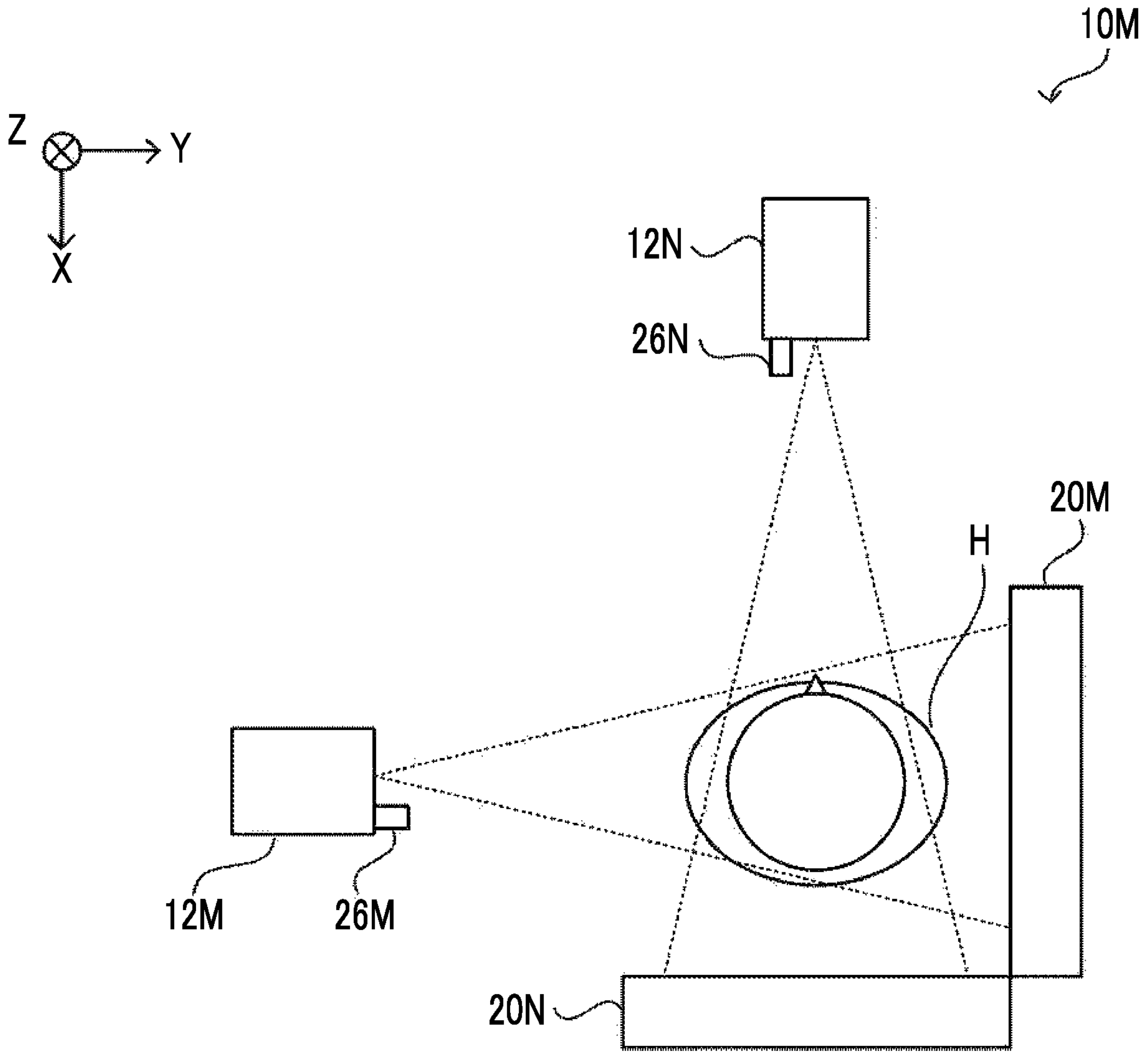
FIG. 12 is a schematic view illustrating another example of the imaging apparatus.
Figure 13:
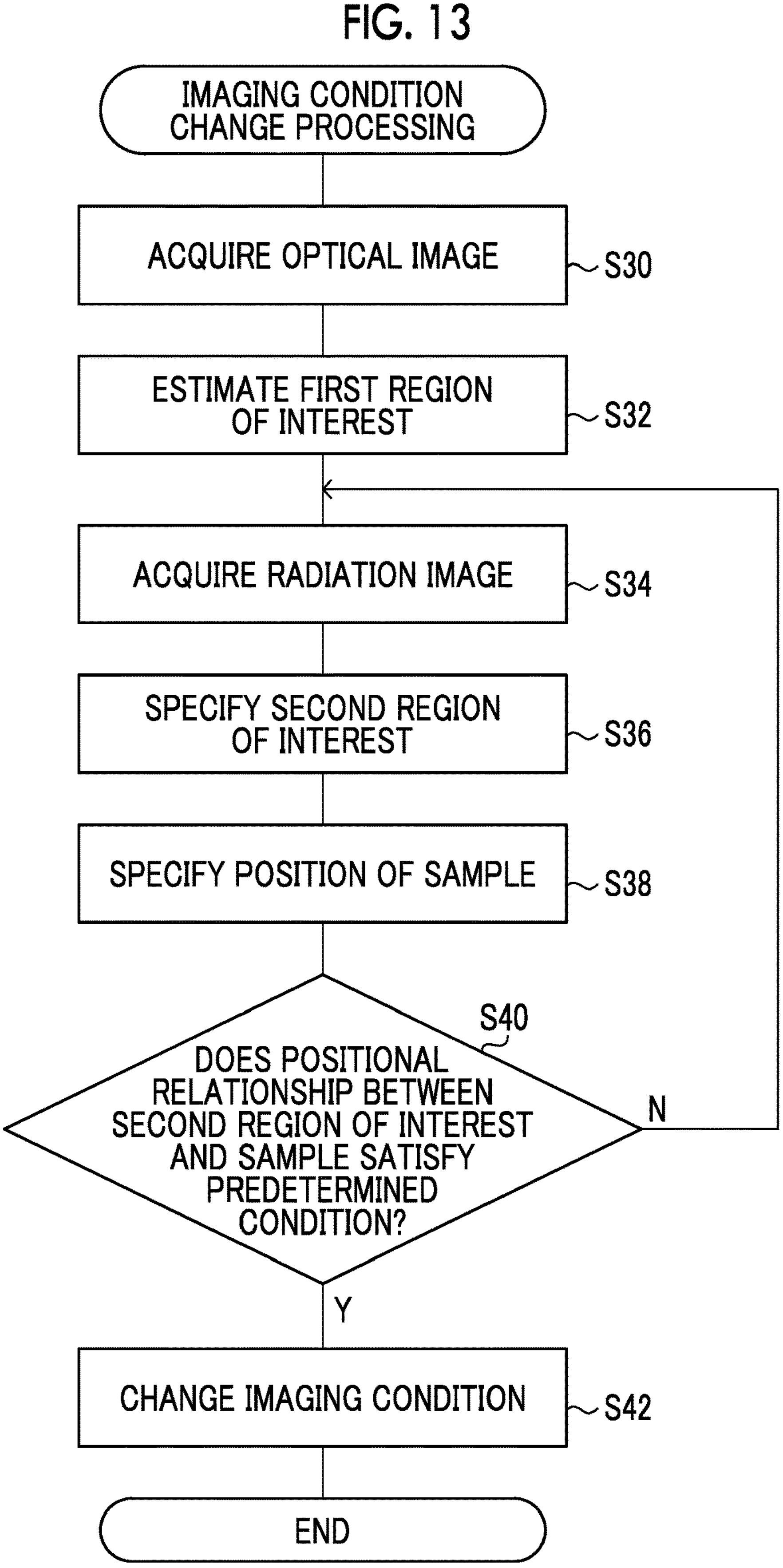
FIG. 13 is a flowchart illustrating an example of imaging condition change processing.

In addition, for example, as illustrated in FIG. 12, an imaging apparatus 10M according to the present embodiment may perform optical imaging and radiography from a second direction (the X direction) that is different from a first direction (the Y direction) simultaneously with the optical imaging and the radiography from the first direction. The imaging apparatus 10M illustrated in FIG. 12 comprises a radiation emitting unit 12M and a radiation detector 20M that perform radiography of the subject H from a side surface side (the first direction), and an optical camera 26M that performs optical imaging. In addition, the imaging apparatus 10M comprises a radiation emitting unit 12N and a radiation detector 20N that perform radiography of the subject H from a front surface side (the second direction), and an optical camera 26N that performs optical imaging.

In this case, each functional unit may perform the same processing as the above optical image 30 and the radiation image 40 for a second optical image and a second radiation image obtained by performing the optical imaging and the radiography from the second direction. Specifically, the acquisition unit 60 may acquire the second optical image and the second radiation image. The estimation unit 62 may estimate a position of at least one third region of interest (for example, the stomach) based on the second optical image acquired by the acquisition unit 60. The specifying unit 64 may specify a fourth region of interest (for example, the stomach) corresponding to the position of the third region of interest that is estimated by the estimation unit 62 in the second radiation image acquired by the acquisition unit 60. In the case of the videofluoroscopic examination of swallowing, similar to the first region of interest described above, the third region of interest and the fourth region of interest are at least one of the throat, the shoulder, the esophagus, the airway, the epiglottis, or the stomach.

In addition, the specifying unit 64 may monitor the position of the sample S based on the second radiation image acquired by the acquisition unit 60. The controller 66 may change the imaging condition of the radiography from at least one of the first direction or the second direction based on the positional relationship between the fourth region of interest specified by the specifying unit 64 and the sample S monitored from the second radiation image. That is, the controller 66 may change the imaging conditions of at least one of the radiation emitting unit 12M or the radiation emitting unit 12N, based on the second radiation image. For example, the controller 66 may first start radiography from the second direction, detect that the sample S has reached the stomach (the fourth region of interest) based on the second radiation image, and then stop radiography from the second direction and switch to radiography from the first direction.

In addition, the controller 66 may notify that the imaging conditions have been changed. For example, in a case in which the radiation image 40 is displayed on the display 54 as illustrated in FIG. 7 after performing radiography by changing the imaging conditions, a message such as "dose has been increased by XX and irradiated" may be displayed.

Next, an action of the console 50 according to the present embodiment will be explained with reference to FIG. 12. In the console 50, the CPU 51 executes the information processing program 57 to execute imaging condition change processing illustrated in FIG. 12. The imaging condition change processing is executed, for example, in a case in which the user gives an instruction to start execution via the operating unit 55.

In step S30, the acquisition unit 60 acquires the optical image of the subject H imaged by the optical camera 26 of the imaging apparatus 10. In step S32, the estimation unit 62 estimates the position of at least one first region of interest, based on the optical image of the subject H acquired in step S30.

In step S34, the acquisition unit 60 acquires a plurality of radiation images of the subject H which are obtained by continuously performing radiography of a state in which the subject H swallows the sample S by the imaging apparatus 10. In step S36, the specifying unit 64 specifies the second region of interest corresponding to the position of the first region of interest estimated in step S32 in the radiation image acquired in step S34. In step S38, the specifying unit 64 specifies the position of the sample S in the radiation image acquired in step S34.

In step S40, the controller 66 determines whether or not the positional relationship between the second region of interest specified in step S36 and the sample S specified in step S38 satisfies a predetermined condition (for example, whether or not the sample S has entered the region of the shoulder). In a case in which the determination in step S40 is a negative determination, that is, in a case in which the positional relationship between the second region of interest and the sample S does not satisfy the predetermined condition, the processing returns to step S34 and the monitoring of the position of the sample S in the radiation image is continued. On the other hand, in a case in which the determination in step S40 is an affirmative determination, that is, in a case in which the positional relationship between the second region of interest and the sample S satisfies a predetermined condition, the processing proceeds to step S42. In step S42, the controller 66 controls to change the imaging conditions for radiography, and ends the main imaging condition change processing.

As explained above, the console 50 according to an aspect of the present disclosure comprises at least one processor, in which the processor is configured to acquire at least one optical image obtained by optically imaging the subject H from the first direction, estimate the position of at least one first region of interest based on the optical image, acquire the plurality of radiation images obtained by continuously performing radiography of a state in which the subject H swallows the sample S from the first direction, specify the second region of interest corresponding to the position of the first region of interest in the radiation image, monitor the position of the sample S based on the plurality of radiation images, and change the imaging conditions for the radiography based on the positional relationship between the second region of interest and the sample S.

That is, with the console 50 according to the present embodiment, the position of the region of interest can be estimated based on the optical image even in a case in which the region of interest (for example, the shoulder), which is a boundary for changing the imaging conditions, cannot be specified with the radiation image alone. Therefore, the imaging conditions such as the dose can be appropriately switched, and the imaging of the radiation image can be supported.

Figure 14:
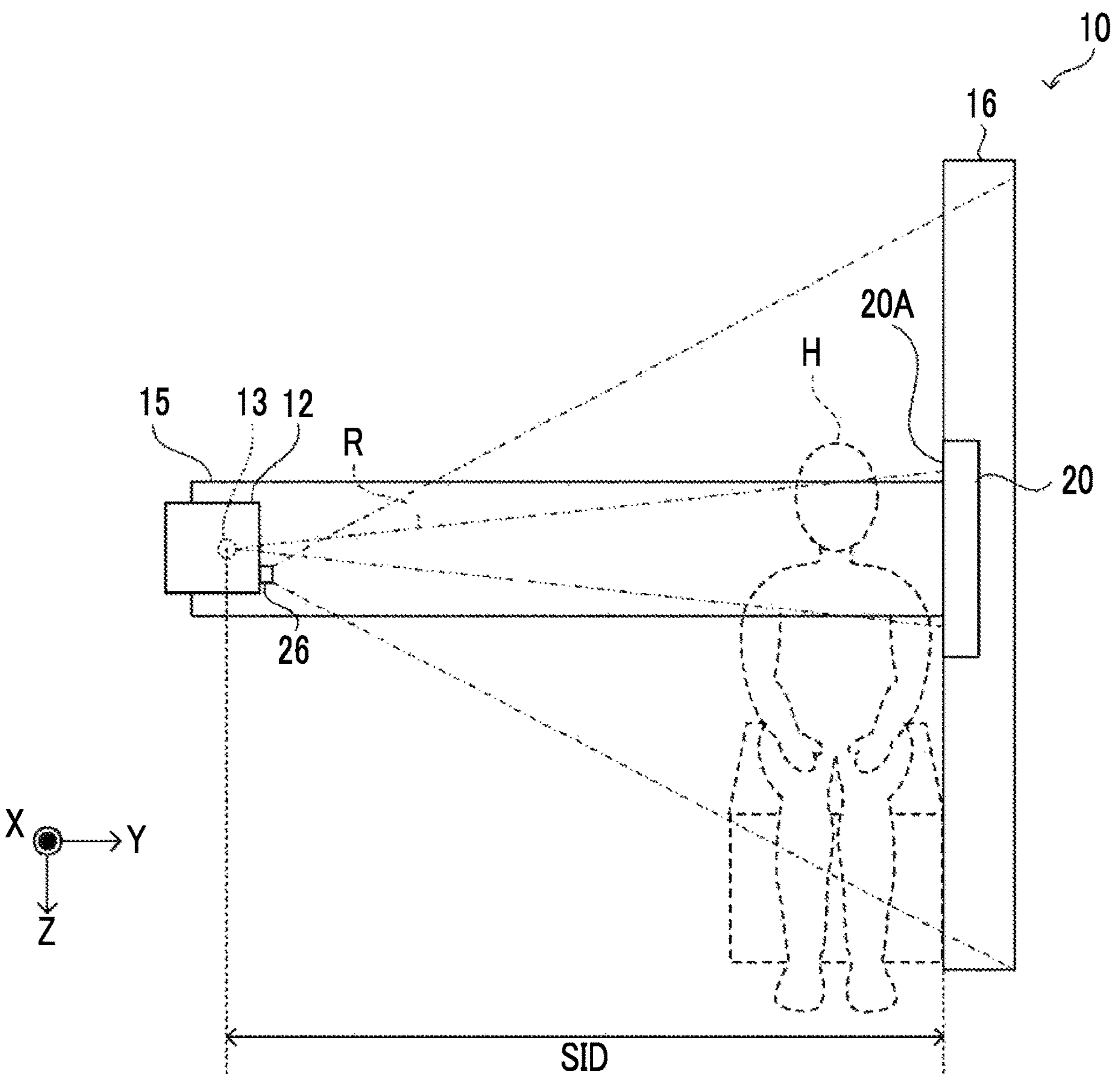
FIG. 14 is a side view illustrating an example of an external apparatus of another form of the imaging apparatus.

In addition, in each of the above-described embodiments, as explained with reference to FIG. 2, an aspect in which the radiation source 13 and the radiation detector 20 are both movable in the imaging apparatus 10 and the SID is variable has been explained, but the present disclosure is not limited to this. The technology of the present disclosure can be applied to a radiography apparatus of forms other than the imaging apparatus 10 as illustrated in FIG. 2. For example, as illustrated in FIG. 14, the radiation source 13 and the radiation detector 20 are connected by an arm 15, and the positional relationship between the radiation source 13 and the radiation detector 20 and the SID may be fixed or semi-fixed (variable within a predetermined range). Examples of the imaging apparatus include a C-arm type radiography apparatus, an X-ray television, and the like.

In addition, for example, either one of the radiation source 13 or the radiation detector 20 may be movable, and the other may be in a non-movable form. Examples of the imaging apparatus include a form in which a ceiling-mounted type radiation source 13 and an imaging table having the radiation detector 20 disposed in an imaging room are combined, and the like. The imaging table, in this case, may have a radiation detector 20 inside the imaging s table in a non-detachable manner, or may have a holder in which the radiation detector 20 (electronic cassette) is accommodated in a detachable manner. In addition, for example, the position of the holder (radiation detector 20) may be variable within a predetermined range.

In addition, for example, although an aspect of imaging the subject H in a sitting posture has been explained in FIG. 2 and FIG. 14, the present disclosure is not limited to this, and for example, the subject H in the upright posture may be imaged, or a decubitus imaging table may be provided and the subject H in the decubitus posture may be imaged. In addition, the size of the radiation detector 20 is not particularly limited, and for example, it may be one for long-length imaging.

In addition, in each of the above-described embodiments, as illustrated in FIG. 2, the center of the radiation detector 20 has been explained as being registered with the irradiation axis Ar of the radiation R emitted from the radiation source 13, but the present disclosure is not limited to this. For example, in a case in which a portable electronic cassette is used as the radiation detector 20, the center of the radiation detector 20 and the irradiation axis Ar of the radiation R may deviate. In addition, in the geometric calculation using the SID, the positional relationship (intervals dx, dy, and dz) between the radiation source 13 and the optical camera 26, the angle of view w of the optical camera 26, and the like, there may be misregistration between the optical image and the radiation image. Therefore, for example, a marker for registration is provided in the radiation detector 20, and the specifying unit 64 may perform the registration of the optical image and the radiation image based on the marker included in the optical image obtained by imaging the radiation detector 20 by the optical camera 26.

In addition, in each of the above-described embodiments, the explanation has been made in which the optical image is captured using the optical camera 26 included in the imaging apparatus 10, and the positional relationship (intervals dx, dy, and dz) between the radiation source 13 and the optical camera 26 is predetermined, but the present disclosure is not limited to this. For example, instead of the optical camera 26 included in the imaging apparatus 10, an external camera such as a digital camera or a camera of a smartphone may be used to capture the optical image. In this case, since the positional relationship between the radiation source 13 and the camera fluctuates, the registration of the optical image and the radiation image using the above-described geometric calculation is difficult. Therefore, for example, a marker for registration is provided in the radiation detector 20, and the specifying unit 64 may perform the registration of the optical image and the radiation image based on the marker included in the optical image obtained by imaging the radiation detector 20 by the external camera.

In addition, in each of the above-described embodiments, an aspect in which the body thickness of the subject H is specified based on the optical image has been explained, but the present disclosure is not limited to this. For example, the body thickness of the subject H may be specified using a distance-measuring sensor such as laser imaging detection and ranging or light detection and ranging (LIDAR), a time of flight (TOF) camera, a stereo camera, or the like.

In addition, in each of the above-described embodiments, for example, as hardware structures of processing units that execute various types of processing, such as the acquisition unit 60, the estimation unit 62, the specifying unit 64, and the controller 66, various processors illustrated below can be used. The above-described various processors include a programmable logic device (PLD) that is a processor of which the circuit configuration can be changed after manufacture, such as a field programmable gate array (FPGA), a dedicated electrical circuit that is a processor having circuit configuration dedicatedly designed to perform specific processing, such as an application specific integrated circuit (ASIC), and the like, in addition to the CPU that is a general-purpose processor functioning as various processing units by executing software (program) as described above.

One processing unit may be formed of one of these various processors, or may be formed of a combination of two or more processors of the same type or different types (for example, a combination of a plurality of FPGAs or a combination of a CPU and an FPGA). In addition, a plurality of processing units may be formed of one processor.

As an example in which a plurality of processing units are formed of one processor, first, there is an aspect in which one processor is formed of a combination of one or more CPUs and software as typified by a computer, such as a client or a server, and functions as a plurality of processing units. Second, there is a form in which, as typified by a system on chip (SoC) and the like, a processor that implements functions of the entire system including the plurality of processing units with one integrated circuit (IC) chip is used. In this way, various processing units are formed using one or more of the above-described various processors as hardware structures.

Furthermore, more specifically, electrical circuitry in which circuit elements, such as semiconductor elements, are combined can be used as the hardware structures of these various processors.

In addition, in the above-described embodiment, an aspect in which the information processing program 57 in the console 50 is pre-stored in the storage unit 52 has been explained, the present disclosure is not limited thereto. The information processing program 57 may be provided in a form in which the information processing program 57 is recorded in recording mediums, such as a compact disc read only memory (CD-ROM), a digital versatile disc read only memory (DVD-ROM), and a universal serial bus (USB) memory. In addition, the information processing program 57 may be downloaded from an external device through a network. Furthermore, the technology of the present disclosure extends to a storage medium for non-temporarily storing the program, in addition to the program.

The technology of the present disclosure can be appropriately combined with the above-described embodiment and examples. The description contents and the illustrated contents above are the detailed explanations of the parts according to the technology of the present disclosure, and are merely examples of the technology of the present disclosure. For example, the above explanations related to configurations, functions, actions, and effects are explanations related to examples of configurations, functions, actions, and effects of the parts according to the technology of the present disclosure. Therefore, it is needless to say that unnecessary parts may be deleted, or new elements may be added or replaced with respect to the description contents and illustrated contents above, within a scope not departing from the spirit of the technology of the present disclosure.

What is claimed is:

1. An information processing apparatus comprising at least one processor, wherein the processor is configured to:
- acquire at least one optical image obtained by optically imaging a subject from a first direction;
- estimate a position of at least one first region of interest based on the optical image;
- acquire a plurality of radiation images obtained by continuously performing radiography of a state in which the subject swallows a sample from the first direction;
- specify a second region of interest corresponding to the position of the first region of interest in the radiation image;
- monitor a position of the sample based on the plurality of radiation images;
- change an imaging condition for the radiography based on a positional relationship between the second region of interest and the sample;
- determine whether the subject is in a forward leaning posture, an upright posture, or a backward leaning posture, based on the optical image; and
- store the radiation image and a determination result of the posture of the subject in a storage unit in association with each other.

2. The information processing apparatus according to claim 1, wherein the processor is configured to:
- specify a body thickness of the subject based on the optical image; and
- change the imaging condition based on the body thickness.

3. The information processing apparatus according to claim 1, wherein the processor is configured to:
- specify an imaging direction of the subject based on the optical image; and
- change the imaging condition based on the imaging direction.

4. The information processing apparatus according to claim 1, wherein the processor is configured to notify that the imaging condition is changed.

5. The information processing apparatus according to claim 1, wherein the processor is configured to display the radiation image and a type of the second region of interest in which the sample included in the radiation image is located, on a display in association with each other.

6. The information processing apparatus according to claim 1, wherein the processor is configured to store the radiation image and a type of the second region of interest in which the sample included in the radiation image is located, in a storage unit in association with each other.

7. The information processing apparatus according to claim 1, wherein the processor is configured to:
- specify a plurality of joint points of the subject based on the optical image; and
- estimate the position of the first region of interest based on a relative positional relationship of the plurality of joint points.

8. The information processing apparatus according to claim 1, wherein the first region of interest and the second region of interest are at least one of a throat, a shoulder, an esophagus, an airway, an epiglottis, or a stomach.

9. The information processing apparatus according to claim 1, wherein the processor is configured to:
- acquire a second optical image and a second radiation image which are obtained by performing optical imaging and radiography from a second direction that is different from the first direction simultaneously with the optical imaging and the radiography from the first direction;
- estimate a position of at least one third region of interest based on the second optical image;
- specify a fourth region of interest corresponding to the position of the third region of interest in the second radiation image;

monitor the position of the sample based on the second radiation image; and change the imaging condition for the radiography from at least one of the first direction or the second direction, based on a positional relationship between the fourth region of interest and the sample that is monitored from the second radiation image.

10. The information processing apparatus according to claim 1, wherein:

the radiation image is an image captured by an imaging apparatus in which a distance between a radiation source and a radiation detector is variable, and the processor is configured to:

acquire the distance between the radiation source and the radiation detector; and specify the second region of interest in the radiation image based on the distance.

11. The information processing apparatus according to claim 10, wherein:

the imaging apparatus includes a radiation emitting unit of ceiling-mounted type, and the radiation emitting unit includes the radiation source.

12. An information processing method comprising:

acquiring at least one optical image obtained by optically imaging a subject from a first direction;

estimating a position of at least one first region of interest based on the optical image;

acquiring a plurality of radiation images obtained by continuously performing radiography of a state in which the subject swallows a sample from the first direction;

specifying a second region of interest corresponding to the position of the first region of interest in the radiation image;

monitoring a position of the sample based on the plurality of radiation images;

changing an imaging condition for the radiography based on a positional relationship between the second region of interest and the sample;

determining whether the subject is in a forward leaning posture, an upright posture, or a backward leaning posture, based on the optical image; and storing the radiation image and a determination result of the posture of the subject in a storage unit in association with each other.

13. A non-transitory computer-readable storage medium storing an information processing program for causing a computer to execute a process comprising:

acquiring at least one optical image obtained by optically imaging a subject from a first direction;

estimating a position of at least one first region of interest based on the optical image;

acquiring a plurality of radiation images obtained by continuously performing radiography of a state in which the subject swallows a sample from the first direction;

specifying a second region of interest corresponding to the position of the first region of interest in the radiation image;

monitoring a position of the sample based on the plurality of radiation images;

changing an imaging condition for the radiography based on a positional relationship between the second region of interest and the sample;

determining whether the subject is in a forward leaning posture, an upright posture, or a backward leaning posture, based on the optical image; and storing the radiation image and a determination result of the posture of the subject in a storage unit in association with each other.

* * * * *